United States Patent [19]

Christian et al.

[11] Patent Number: 5,366,466
[45] Date of Patent: Nov. 22, 1994

[54] SURGICAL SCISSORS

[75] Inventors: Jeffrey J. Christian; Christina W. Forston, both of San Jose, Calif.

[73] Assignee: Unisurge, Inc., Cupertino, Calif.

[21] Appl. No.: 911,871

[22] Filed: Jul. 9, 1992

[51] Int. Cl.$^5$ ............................................ A61B 17/32
[52] U.S. Cl. .................................... 606/174; 606/170
[58] Field of Search ............... 606/167, 170, 174, 51, 606/52, 205-211; 128/750-755, 3-6

[56] References Cited

U.S. PATENT DOCUMENTS

| | | |
|---|---|---|
| 5,071,412 | 12/1991 | Noda . |
| 5,147,357 | 9/1992 | Rose et al. ............................ 606/51 |
| 5,152,778 | 10/1992 | Bales, Jr. et al. .................. 606/174 |
| 5,209,755 | 5/1993 | Abraham et al. .................. 606/205 |

FOREIGN PATENT DOCUMENTS 0021797  1/1893  United Kingdom ................. 606/174

9102493  3/1991  WIPO ................................. 606/174

*Primary Examiner*—Stephen C. Pellegrino
*Assistant Examiner*—William Lewis
*Attorney, Agent, or Firm*—Flehr, Hohbach, Test, Albritton & Herbert

[57] ABSTRACT

Surgical scissors having first and second blades with cutting edges. A housing is provided. The first and second blades are pivotally mounted in the housing to permit movement between open and closed positions. First and second linkage arms are provided and are pivotally connected to the first blade and to the second blade. A push-pull rod is slidably mounted in the housing and has a distal extremity. The distal extremity of the push-pull rod is pivotally connected to the first and second linkage arms for moving the blades between open and closed positions as the push-pull rod is moved rectilinearly.

5 Claims, 2 Drawing Sheets

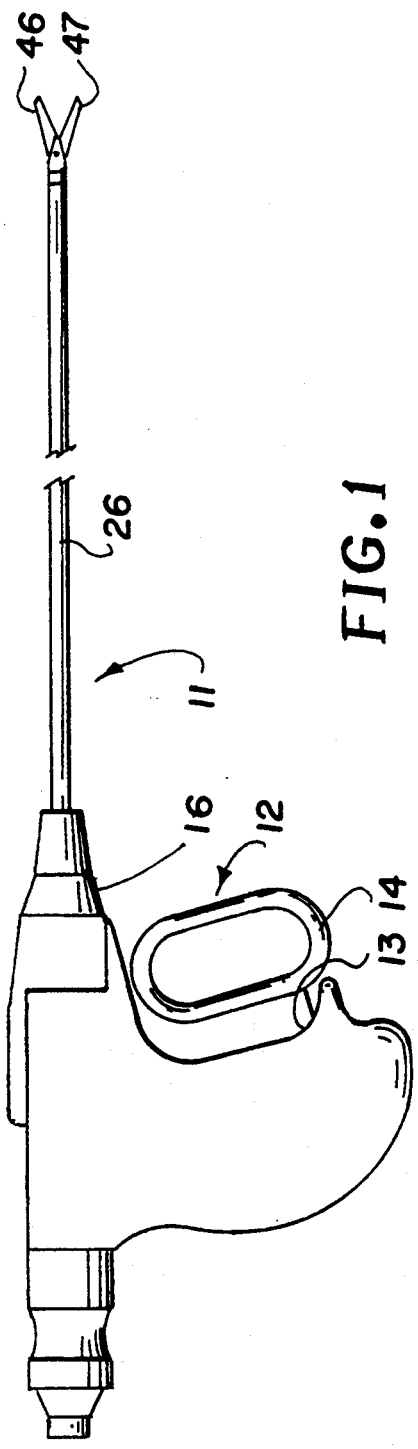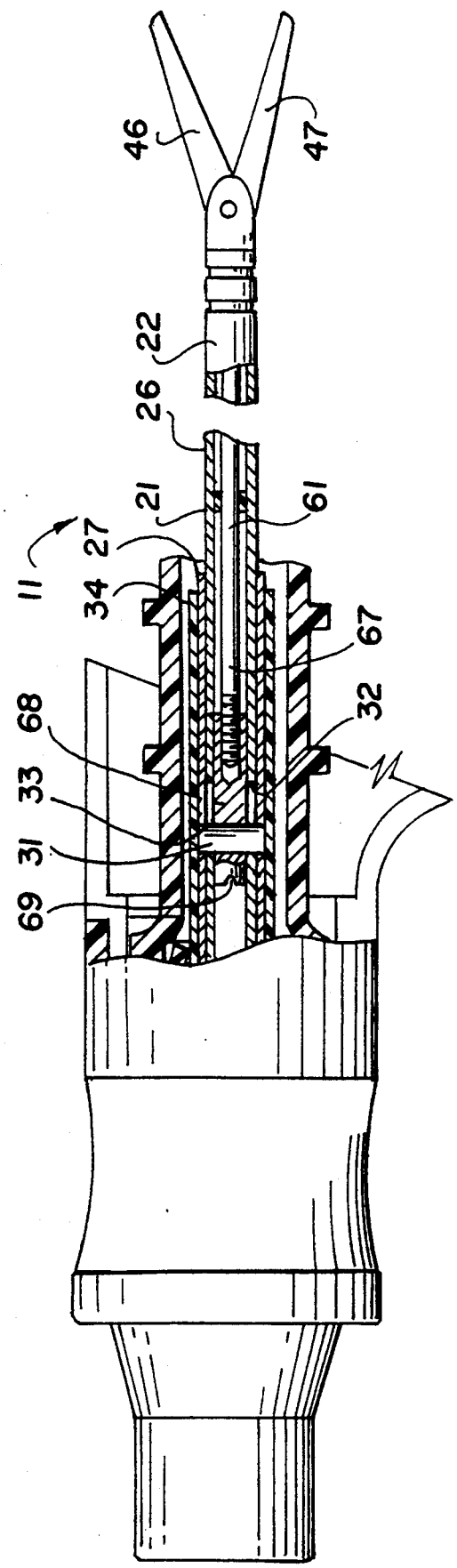

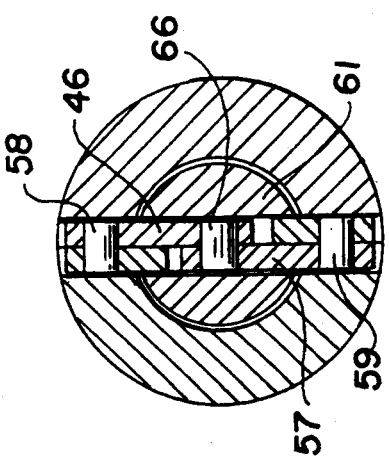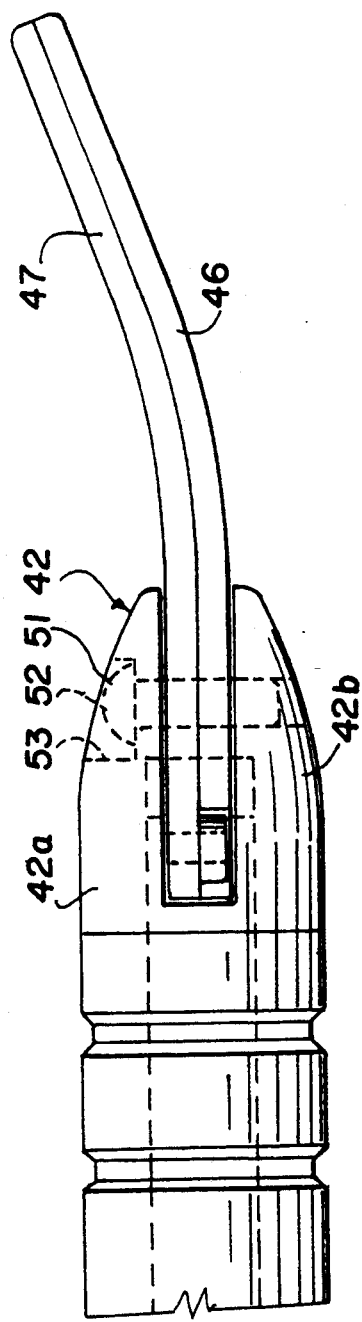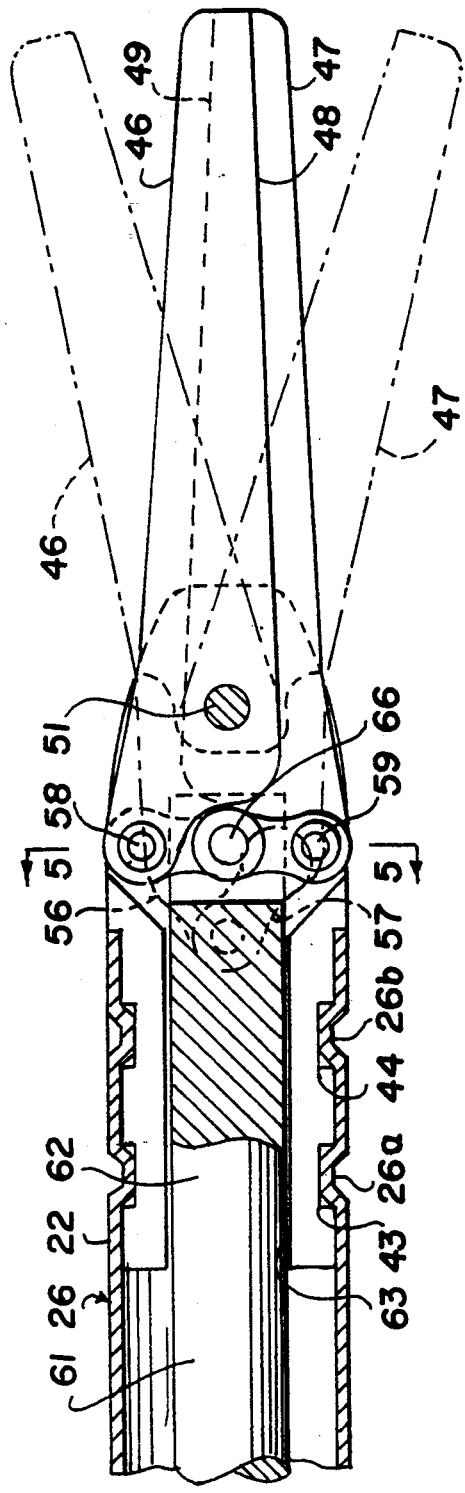

SURGICAL SCISSORS

This invention relates to a surgical scissors and more particularly to a surgical scissors for use with a hand-held surgical device for use in endoscopic and laparoscopic procedures.

Surgical scissors heretofore have been provided, and in particular surgical scissors have been provided for use in laparoscopic surgery. However, it has been found that such scissors are very delicate and often are unable to withstand the rigors of surgery for any period of time. There is, therefore, a need for a new and improved surgical scissors to overcome these disadvantages.

In general, it is an object of the present invention to provide a surgical scissors which is robust, sharp and cuts very well.

Another object of the invention is to provide a surgical scissors of the above character which can be utilized with a hand-held surgical device in endoscopic and laparoscopic procedures.

Additional objects and features of the invention will appear from the following description in which the preferred embodiments are set forth in detail in conjunction with the accompanying drawings.

FIG. 1 is a side elevational view of a surgical hand-held device having mounted therein the surgical scissors of the present invention for use in conjunction therewith.

FIG. 2 is a view partially in cross-section of the surgical scissors shown in FIG. 1.

FIG. 3 is a partial side elevational view of the surgical scissors shown in FIG. 2 looking along the line 3—3 of FIG. 2.

FIG. 4 is a view partially in cross-section of the distal extremity of the surgical scissors shown in FIGS. 2 and 3.

FIG. 5 is a cross-sectional view taken along the line 5—5 of FIG. 4.

In general, the surgical scissors of the present invention consists of first and second blades having cutting edges. Means is provided for pivotally interconnecting the first and second blades to permit movement of the first and second blades between open and closed positions. First and second linkage arms are provided. Means is provided for connecting the first linkage arm to the first blade and for pivotally connecting the second linkage arm to the second blade. A push-pull rod having a distal extremity is provided. Means is provided for pivotally connecting the distal extremity of the push-pull rod to the first and second linkage arms.

More specifically, as shown in FIGS. 1–5 of the drawings, the surgical scissors 11 incorporating the present invention is removably mounted in a hand-held device 12 of the type described in co-pending application Ser. No. 07/806,666 filed on Dec. 13, 1991. As described therein, it consists of a housing 13 which is provided with a trigger bar 14 that is utilized for causing rectilinear movement of an actuator tube assembly (not shown) and a knob 16 for causing a rotation of the same as described therein.

The surgical scissors 11 of the present invention is formed as a tool which is adapted to be used in conjunction with the hand-held device 12 and in many respects is constructed in a manner similar to other tools described is said co-pending application Ser. No. 07/806,666 filed on Dec. 13, 1991.

The surgical scissors 11 is like one of the tools said co-pending application Ser. No. 07/806,666 filed on Dec. 13, 1991, with a proximal extremity 21 substantially identical to the proximal extremity shown in said co-pending application. The distal extremity 22 of the surgical scissors 11 is provided by an elongate inner tubular member 26 which is mounted for rectilinear movement in an outer tubular member 27. A cylindrical pin 31 extends transversely of the inner tubular member 26 and extends through aligned parallel slots 32 provided in the tubular member 26. The pin 31 is seated in holes 33 provided in the outer tubular member 27. The pin 31 is retained therein by a plastic shrink tube 34.

A scissors mechanism 41 is mounted on the distal extremity 22 and consists of a nose 42 which is formed of two parts 42a and 42b. The nose parts 42a and 42b are provided with spaced apart, annular recesses 43 and 44, and are retained within the distal extremity of the scissors 11 by having portions 26a and 26b of the inner tubular member 26 crimped therein, as shown particularly in FIGS. 3 and 4.

The scissors mechanism 41 consists of first and second blades 46 and 47 having straight cutting edges 48 and 49. Means is provided for pivotally interconnecting the first and second blades 46 and 47 to permit pivotal movement between open and closed positions and for mounting the same in the nose 42 and consists of a pivot screw 51 could also be a rivet. The pivot screw 51 has its head 52 recessed within a hole 53 provided in the nose part 42a and has its other end threaded into the nose part 42b. As shown in FIG. 3, the blades 46 and 47 are curved slightly at their outer extremities in a direction away from the axis of the tubular member 26 and lie generally parallel to each other.

First and second linkage arms 56 and 57 are provided. Means is provided for pivotally connecting one or the first end of the linkage arm 56 to the first blade 46 and consists of a pin 58. Means is also provided for connecting one or the first end of the linkage rod 57 to the blade 47 and consists of a pin 59.

The surgical scissors 11 is provided with a push-pull rod 61 mounted within the inner tubular member 26 for rectilinear movement therein. It is provided with a distal extremity 62 which is slidably mounted in a bore 63 provided in the nose 42. Means is provided for pivotally connecting the distal extremity 62 of the push-pull rod 61 to the other or second ends of the linkage arms 56 and 57 and consists of a pin 66. The proximal extremity 67 of the push-pull rod 61 is threaded, as shown, and is threaded into a cylindrical member 68 (see FIG. 2) which is provided with a screwdriver receiving notch 69 to permit the cylindrical member 68 to be threaded onto the proximal extremity 67 of the push-pull rod 61. The cylindrical member 68 is pivotally mounted on the pin 31 hereinbefore described.

Operation and use of the surgical scissors may now be briefly described as follows. Let is be assumed that it is desired to perform a cutting action in connection with an endoscopic or laparoscopic procedure. Let it also be assumed that the surgical scissors 11 has been placed in the hand-held device 12. Operation of the trigger bar 14 will cause opening and closing of the scissor blades 46 and 47 between the open and closed positions as shown in FIGS. 2 and 4. The operation of the trigger bar causes rectilinear movement of the push-pull rod 61 in the manner described in co-pending application Ser. No. 07/806,666 filed Dec. 13, 1991. The linkage arms 56 and 57 are configured in such a manner so that as the push-pull rod 61 is pushed forwardly toward the distal extremity, the toggle-type mechanism which is created by the linkage arms 56 and 57 is moved to a substantially vertical orientation as shown in FIG. 4 to cause the blades 46 and 47 to move towards the closed position.

By utilizing such a toggle-type mechanism, it is possible to achieve an optimum toggle mechanical advantage to create the greatest cutting force as the blades approach the closed position. The finest resolution of the scissors 11 is achieved as the toggle mechanism reaches a substantially vertical position and as the cutting blades 46 and 47 come to a closed position. As the optimum mechanical action is being achieved, the push-pull rod as it nears the end of its travel is travelling the greatest amount of distance for the least amount of scissor blade travel. Since the optimum mechanical advantage is achieved near the closed position of the scissor blades 46 and 47, the physician or surgeon utilizing the scissors achieves an "optimum feel" in a tactile sense while operating the trigger bar 14. This makes it possible for the physician or surgeon to readily perform progressive snipping of tissue with the distal extremities of the blades 46 and 47. In this way, the surgeon can progressively snip through tissue with great precision and with a precise cutting action. The scissors of the present invention makes this advantageous because the best resolution of the scissors is up near the tip.

From the foregoing, it can be seen that there has been provided a surgical scissors which performs very well in the hands of the surgeon. Its cutting action is smooth and precise. In addition, the scissors is robust so that it can withstand repeated use while still performing precision cutting or snipping. The cutting blades 46 and 47 are provided with cutting edges which remain sharp. The surgical scissors is of a type which can be utilized with hand-held devices for use in endoscopic and laparoscopic procedures.

What is claimed is:

1. In a surgical scissors, first and second blades having cutting edges and having proximal and distal extremities, a tubular member having proximal and distal extremities, the distal extremity having an open end, the tubular member having an outer diameter, a nose mounted in the open end of the tubular member and having a diameter no greater than the outer diameter of the tubular member, means carried by the nose pivotally interconnecting said first and second blades between the proximal and distal extremities of the first and second blades within the nose to permit movement of the first and second blades between open and closed positions, first and second linkage arms disposed within the nose, means in the nose pivotally connecting the first linkage arm to the proximal extremity of the first blade, means in the nose pivotally connecting the second linkage arm to the proximal extremity of the second blade, a push-pull rod slidably mounted in the tubular member and in the nose and having a distal extremity and means in the nose pivotally connecting the distal extremity of the push-pull rod to the first and second linkage arms for moving the blades between open and closed positions as the push-pull rod is moved rectilinearly, the proximal extremities of said first and second blades being positioned with respect to the means pivotally interconnecting the first and second blades so that as said push-pull rod is pushed, said cutting edges will be moved to a closed position.

2. A scissors as in claim 1 wherein said nose is formed of first and second parts, and wherein said first and second blades are pivotally mounted between said first and second parts.

3. A scissors as in claim 1 wherein said linkage arms and said first and second blades lie parallel to each other.

4. A scissors as in claim 1 wherein said first and second linkage arms form a toggle mechanism to provide a toggle mechanical advantage upon movement of the cutting edges of the blades toward the closed position.

5. In a surgical scissors, first and second blades having cutting edges and having proximal and distal extremities, a sleeve nose, means mounted on said housing pivotally interconnecting said first and second blades between the proximal and distal extremities to permit movement between open and closed positions, first and second linkage arms, means pivotally connecting the first linkage arm to the proximal extremity of the first blade, means pivotally connecting the second linkage arm to the proximal extremity of the second blade, a push-pull rod slidably mounted for rectilinear movement in the housing and having a distal extremity and means pivotally connecting the distal extremity of the push-pull rod to the first and second linkage arms for moving the blades between open and closed positions as the push-pull rod is moved rectilinearly, the proximal extremities of said first and second blades being positioned with respect to the means pivotally interconnecting the first and second blades so that as said push-pull rod is pushed, said cutting edges will be moved to a closed position, said first and second linkage arms forming a toggle mechanism to provide a toggle mechanical advantage upon movement of the cutting edges of the blades toward the closed position, said toggle mechanism being configured so that as said first and second linkage arms approach generally aligned positions at substantially right angles to the direction of movement of the push-pull rod, the cutting edges near their closed positions to apply the greatest cutting force.

* * * * *